United States Patent [19]

Pelyva et al.

[11] Patent Number: 4,983,764

[45] Date of Patent: Jan. 8, 1991

[54] PROCESS FOR PREPARING N-PHOSPHONOMETHYL-GLYCINE

[75] Inventors: Jenő Pelyva; László Lendvai, both of Füzfőgyártelep; Sándor Bálint, Balatonalmádi; Zoltán Kolonics, Balatonalmádi; Csaba Söptei, Veszprém; Sándor László, Füzfőgyártelep; Béla Karácsonyi, Budapest; Jánosné Benczik, Balatonalmádi; Csaba Kayos; Sándor Silye, both of Veszprém, all of Hungary

[73] Assignee: Nitrokemia Ipartelepek, Hungary

[21] Appl. No.: 426,106

[22] Filed: Oct. 24, 1989

[30] Foreign Application Priority Data

Nov. 2, 1988 [HU] Hungary ............................ 5676/88

[51] Int. Cl.$^5$ ............................................. C07F 9/38
[52] U.S. Cl. ..................................................... 562/17
[58] Field of Search ........................................... 562/17

[56] References Cited

U.S. PATENT DOCUMENTS 3,950,402  4/1976  Franz ..................................... 562/17
3,954,848  5/1976  Franz ..................................... 562/17

FOREIGN PATENT DOCUMENTS 127415  11/1978  Japan ..................................... 562/17

Primary Examiner—J. E. Evans

[57] ABSTRACT

The invention relates to an improvement of a process for preparing N-phosphonomethyl-glycine by oxydation of N-phosphonomethyl-imino-diacetic acid in an aqueous sulphuric acidic medium with hydrogen peroxide.

A characteristic feature is using a waste acid liquor as reaction medium formed as aqueous sulphuric acid and obtained after the separation of N-phosphonomethyl-glycine when carrying out oxydation. This solution is optionally diluted with water until a concentration of 12–18 weight % of sulphuric acid and 3–5 weight % of N-phosphonomethyl-glycine.

6 Claims, No Drawings

PROCESS FOR PREPARING N-PHOSPHONOMETHYL-GLYCINE

The invention relates to the preparation of N-phosphonomethyl-glycine by oxidising N-phosphonomethyl-imino diacetic acid with hydrogen peroxide in a sulphuric acidic medium. N-phosphonomethyl-glycine (glyphosate) is an important active ingredient of different herbicidal compositions.

Several processes are known in the art according to which N-phosphonomethyl-imino diacetic acid is oxidised into N-phosphonomethyl-glycine in an acidic medium by using hydrogen peroxide. According to the process described in Dutch Pat. specification No. 7 307 449 N-phosphonomethyl-imino diacetic acid is oxidised into N-phosphonomethyl-glycine with hydrogen peroxide in the presence of an acid, preferably sulphuric acid at a temperature of 40°-100° C. Disadvantage of the process is that acidic waste liquor is forming in great amount in addition to the end product, the processing of which is very expensive and pollutes the environment.

N-phosphonomethyl-imino diacetic acid is oxidised into N-phosphonomethyl-glycine also by using hydrogen peroxide in a manner that oxydation is carried out in acid-free aqueous medium in the presence of different metal-salt catalysts. Disadvantage of this process is that the operation steps require long time, the product can be obtained after evaporation and in addition the metal-salt catalyst may pollute the product.

Summarising the disadvantages of the known processes it can be stated, that the acid, used during oxydation in a sulphuric acidic medium, more or less is influencing the decomposition of the peroxide (first of all the hydrogen peroxide) in every case and during this decomposition by-products are formed which are disadvantageous concerning the main reaction and cannot be oxidised. This significantly increases the chemical reagent requirement of the process and also the costs of materials being necessary for the process. The processing of the strongly acidic reaction mixture is difficult, the acid cannot be regenerated from the reaction mixture, and the waste water of the production can be removed into the environment only after previous neutralization. Further problems may arise from the fact that the end product dissolves in the strongly acidic reaction mixture much better than in water. Considering that the strongly acidic reaction mixtures (first of all the sulphuric acidic solutions) generally cannot be processed by evaporation, the dissolved N-phosphonomethyl-glycine remained in the mother liquor can be separated only by suitable flocculating substances (generally by alcohols). The use of flocculating substance further increases the production costs and has also the disadvantage that it separates the polluting substances too from the reaction mixture, which substances can be removed from the end product in a difficult manner or they cannot be removed at all.

Object of the invention is an oxydation process carried out with hydrogen peroxide in sulphuric acidic medium, by which the relative amount of acid used to one unit of the end product can significantly be decreased, and at the same time the decomposition of hydrogen peroxide caused by sulphuric acid can be partly eliminated, the amount of the waste water formed decreases at least to its 1/5, moreover the loss of yield caused by the end-product dissolved in the sulphuric acid medium can be decreased, too.

It was recognized that N-phosphonomethyl-imino diacetic acid can preferably be oxidised in aqueous-sulphuric acidic medium with hydrogen peroxide, if sulphuric acidic waste liquor obtained after the separation of N-phosphonomethyl-glycine is used as an oxydation medium.

The process of the invention for preparing N-phosphonomethyl-glycine by oxidising N-phosphonomethyl-imino diacetic acid with hydrogen peroxide in an aqueous sulphuric acidic medium can be characterized by using as a medium the waste acid liquor formed during the oxydation in form of an aqueous sulphuric acid after the separation of the N-phosphonomethyl-glycine.

The composition of the waste acid solution is adjusted to 12-18 weight % of sulphuric acid and 3-5 weight % of N-phosphonomethyl-glycine concentration. According to the invention 4.2 to 4.5 moles of hydrogen peroxide are used for preparing 1 mole of end product. The recycling of waste acid liquor is adjusted to use 0.2 to 0.3 moles of sulphuric acid calculated on 1 mole of end product.

According to the process of the invention N-phosphonomethyl-imino diacetic acid is oxidised with hydrogen peroxide in an aqueous sulphuric acidic medium then after N-phosphonomethyl-glycine is filtered out the N-phosphonomethyl-imino diacetic acid is suspended in the liquid of recycled acid, the obtained suspension is heated to boiling point, then hydrogen peroxide is led under the liquid surface of the obtained suspension. By distillation carried out parallel to the oxydation the medium is concentrated, so the N-phosphonomethyl-glycine obtained at the end of the reaction can be crystallized out by cooling. The sulphuric acidic waste liquid obtained after separating the product—optionally completed by the washing water of N-phosphonomethyl-glycine—is used to the following oxydation. According to the process of the invention the waste solution can be recycled to 7-10 charge without the decrease of the quality of N-phosphonomethyl-glycine.

In the known processes carrying out the oxydation with hydrogen peroxide in sulphuric acidic medium a great amount of acid is required for a suitable reaction rate. This waste acid is removed at the end of the process, its recovery requires much energy and is expensive, too. According to our recognition waste acid—optionally completed by the washing water of N-phosphonomethyl-glycine, without recovery and purification—can be used as reaction medium at the oxydation of N-phosphonomethyl-imino diacetic acid. This fact is surprising, because it was to be expected that those impurities which decrease the quality of the end product would enrich in the waste acid liquor—especially after using it several times as reaction medium. To the contrary it was found that according to the process of the invention, the quality of the obtainable N-phosphonomethyl-glycine does not decrease even in the case when waste acid is recycled several times.

According to the known processes 0.7 to 1.3 moles of sulphuric acid are used for producing 1 mole of end product. In Example 1 of Dutch Pat. specification No. 7,307,449 1.3 moles of sulphuric acid is necessary for preparing 1 mole of N-phosphonomethyl-glycine. To the contrary 0.2-0.3 mole of sulphuric acid is used for preparing 1 mole of end product when carrying out the process of the invention.

Further advantage of the invention is that compared to the known processes less hydrogen peroxide is necessary for preparing a unit amount of crystalline N-phosphonomethyl-glycine. In the known processes 4.7 to 7.8 mole hydrogen peroxide is necessary for preparing 1 mole of crystalline product contrary to the process of the invention where this value is 4.2 to 4.5. The process of the invention utilizes the hydrogen peroxide more advantageously, which enables the decrease of the amount of the oxidising agent. The more advantageous utilization can presumably be ascribed to the fact that oxydation is carried out not in a pure aqueous-sulphuric acidic medium but in the mentioned waste acid liquor and which presumably promotes the advantageous proceeding of the reaction. Hydrogen peroxide is not added to the surface of the reaction mixture but preferably under the liquid surface, most preferably to the lower part of the always used liquid column (mass).

The advantageous utilization of hydrogen peroxide according to the process of the invention was not expected. On the basis of the general experiences it can be predicted that the use of the waste solution as reaction medium would rather increase than decrease the amount of oxidising agent demand. Similarly it could rather be expected from a gaseous and not from a liquid oxidising agent that its use in the inner mass of the reaction medium would advantageously influence the oxidising agent requirement calculated to a unit product.

A further advantage of the process of the invention is that the amount of waste acid liquor calculated to a unit of the end product significantly decreases. By the known aqueous-sulphuric acidic oxydation processes using hydrogen peroxide 3-8 g of acidic waste material will be formed in addition to the 1 g N-phosphonomethyl-glycine. For example in Example 1 of Dutch Pat. specification No. 7,307,449 7.5 g acidic waste liquor is formed in addition to 1 g of N-phosphonomethyl-glycine. To the contrary according to the process of the invention in addition to the 1 g of N-phosphonomethyl-glycine 0.7 to 8 g of acidic waste liquor is formed which is very disadvantageous from the point of view of the environmental protection.

Advantageous features of the process of the invention can be summarized as follows:

the amount of the acid necessary for preparing a unit amount of N-phosphonomethyl-glycine can be significantly decreased, the waste substance emission is lower, the hydrogen peroxide amount necessary for preparing a unit product can be decreased by 20-80% compared to the known processes.

The process according to the invention can he carried out at atmospheric or lower or higher pressure. Keeping identical parameters the decrease of the pressure used involves the decrease of the boiling point of the system, while its increase involves the increase of the temperature. The reaction is carried out at a temperature between 20° and 120° C., preferably at 100°-110° C.

The preparation of N-phosphonomethyl-imino diacetic acid used in the process of the invention is known e.g. from DE-PS3,288,846.

The invention is described in detail in the following non-limiting Examples.

EXAMPLE 1

350 g of 20 weight % (0.72 mole) sulphuric acid and 136 g (0.6 mole) of N-phosphonomethyl-imino-diacetic acid were measured into a four-necked glass flask of 500 ml, equipped with a stirrer, thermometer, adder and cooler. The suspension obtained was heated until boiling point and 180 g of a 34% (1.8 mole) aqueous hydrogen peroxide solution was added during 3 hours through a pipe protruding into the lower part of the liquid column while parallel with the addition 180 g of evaporate was distilled off through a cooler into a receiver. After addition stirring was continued for further 15 minutes while boiling under reflux. N-phosphonomethyl-glycine was crystallized from the obtained reaction mixture by cooling, it was filtered and washed with water. The volume of the waste acid liquor was completed to 300 ml by addition of 30 ml of washing water and 109 g (0.48 mole) of N-phosphonomethyl-imino diacetic acid was added, the obtained suspension was heated until boiling point and 162 g of a 34% (1.62 mole) hydrogen peroxide was added during 3 hours into the lower part of the liquid column, while 130 g of evaporate was distilled out parallelly. After addition of hydrogen peroxide the mixture was further stirred for 15 minutes by boiling and using a reflux. N-phosphonomethyl-glycine was crystallized from reaction mixture by cooling, it was filtered and washed with water.

This operation step was repeated thereafter for six times by completing the volume of the sulphuric acidic waste acid liquor to 300 ml with washing water, 109 g (0.48 mole) of N-phosphonomethyl-imino diacetic acid and 162 g of a 34% hydrogen peroxide were used in every case and 130 g of evaporate was distilled off.

During the process totally 898.9 g (3.96 mole) of N-phosphonomethyl-imino-diacetic acid, 70.0 g sulphuric acid and 1314 g of 34% (13.14 mole) of $H_2O_2$ were used. The total amount of the formed sulphuric acidic waste acid was 380 g and that of the N-phosphonomethyl-glycine was 506.6 g of 96.4% (2.89 mole) which corresponds to a yield of 73%. Boiling point: 202°-204° C.

When preparing 100 g product 14 g cc. $H_2SO_4$ and 261 g of 35% $H_2O_2$ were used and 78 g of acidic waste liquor was formed.

EXAMPLE 2

The process described in Example 1 was followed with the difference that $6 \times 144$ g ($6 \times 1.44$ mole) of 34% hydrogen peroxide was used for oxydation in waste acid liquor and $6 \times 120$ g distillate were distilled off.

According to the process of the invention totally 790 g (3.48 mole) of N-phosphonomethyl-imino diacetic acid, 70 g of sulphuric acid and 1044 g of 34g (10.44 mole) hydrogen peroxide were used. 320 g of sulphuric acidic waste crystallisation mother liquor solution, 440.2 g (2.51 mole) of 96.2% N-phosphonomethyl-glycine were formed, corresponding to a yield of 72.0%. Boiling point: 203° C.

When preparing 100 g product 17 g cc. $H_2SO_4$ and 240 g of 35% $H_2O_2$ were used and 76 g acidic waste liquor was formed.

EXAMPLE 3 (comparative)

According to Example 3 of Dutch Pat. specification No. 7,307,449 to a mixture of 39 parts by weight of water and 39 parts by weight of cc. $H_2SO_4$ 20 parts by weight of N-phosphonomethyl-imino diacetic acid was added. The reaction mixture was heated to 80° C. then 277 parts by weight of 35% of $H_2O_2$ were added during 6.5-7 hours, while maintaining the temperature of the mixture at 77°–81° C. While adding $H_2O_2$ during 4 hours the reaction mixture was completed with further 8×20 parts of N-phosphonomethyl-imino diacetic acid. The reaction mixture was thereafter maintained at a temperature of 80° C. under stirring until the reaction was completed according to the effected analysis by NMR spectrum.

The mixture was them stored overnight at 0° C., the precipitated product was separated, washed with water, filtered and 100 parts by weight of N-phosphonomethyl-glycine was obtained.

When preparing 100 g product 39 g of cc. $H_2SO_4$, 277 g of 35% $H_2O_2$ were used, and 375 g of acidic waste liquor was formed.

EXAMPLE 4

Into an equipment described in Example 1, 360 g of waste acid liquor, obtained during the fifth repetition of the process according to Example 1—after filtration of N-phosphonomethyl-glycine—was measured. This contains 14 weight % of sulphuric acid and 4.1 weight % of N-phosphonomethyl-glycine. 109 g of N-phosphonomethyl-imino diacetic acid was added, the obtained suspension was heated until boiling point and during 3 hours 162 g of 34% hydrogen peroxide was added to the lower part of the liquid column, while at the same time 130 g distillate was distilled off. After finishing addition stirring is continued for further 15 minutes under boiling. N-phosphonomethyl-glycine was crystallized from the reaction mixture by cooling, it was filtered, washed with water and dried. 64.5 g of 97.6% product were obtained. Yield: 77.6% (concerning the added N-phosphonomethyl-imino diacetic acid). Boiling point: 203° C.

When preparing 100 g of 100% product 244 g of 35% $H_2O_2$ were used.

We claim:

1. Process for preparing N-phosphonomethyl-glycine by oxidizing N-phosphonomethyl-imino-diacetic acid in aqueous-sulphuric acidic medium with hydrogen peroxide which comprises using as oxidation medium a waste acid liquor formed during the process and obtained after the separation of N-phosphonomethyl-glycine.

2. A process as claimed in claim 1 which comprises adjusting the composition of the waste acid liquor to a concentration of 12–18 weight % of sulphuric acid and 3–5 weight % of N-phosphonomethyl-glycine by diluting it with water.

3. A process as claimed in claim 1 which comprises washing N-phosphonomethyl-glycine with water after its separation.

4. A process as claimed in claim 3 which comprises using the washing water for diluting the waste acid liquor.

5. A process as claimed in claim 1 which comprises using 4.2 to 4.5 mole of hydrogen peroxide for preparing 1 mole of end product.

6. A process as claimed in claim 1 characterized in that the recycling of the waste acid liquor into the process is regulated by using 0.2–0.3 mole of sulphuric acid for preparing 1 mole of end product.

* * * * *